United States Patent [19]

Garrett et al.

[11] 4,223,813

[45] Sep. 23, 1980

[54] NONCRITICALLY ALIGNED VALVING DEVICES FOR FLOW RATE-LIMITING CASSETTES USED IN INTRAVENOUS SOLUTION ADMINISTERING EQUIPMENT

[75] Inventors: Scott T. Garrett, Highland Park; Thurman S. Jess, Mundelein; Vincent L. Knigge, Mundelein; Lee K. Kulle, Mundelein; William L. Rudzena, McHenry; Nick Zissimopoulos, Schaumburg, all of Ill.

[73] Assignee: Baxter Travenol Laboratories, Inc., Deerfield, Ill.

[21] Appl. No.: 878,847

[22] Filed: Feb. 17, 1978

[51] Int. Cl.$^2$ .............................................. A61M 5/14
[52] U.S. Cl. .................................... 222/447; 222/450; 128/214 R; 251/61.1
[58] Field of Search ............ 128/214 R, 214 C, 214.2, 128/227; 251/61.1, 331; 222/207, 206, 212, 214, 447, 450, 451, 452, 440, 445, 449, 55

[56] References Cited

U.S. PATENT DOCUMENTS

| | | | |
|---|---|---|---|
| 3,269,410 | 8/1966 | Alvarado et al. | 251/331 X |
| 3,515,169 | 6/1970 | Berg et al. | 251/331 X |
| 3,666,230 | 5/1972 | Pauliukonis | 251/331 X |
| 4,121,584 | 10/1978 | Turner et al. | 222/450 X |
| 4,142,523 | 3/1979 | Stegeman | 222/55 X |

*Primary Examiner*—David A. Scherbel
*Attorney, Agent, or Firm*—Paul C. Flattery; John P. Kirby, Jr.; Garrettson Ellis

[57] ABSTRACT

Valving configurations between the valve seat in a cassette and the valve members in a controller used to limit the flow rate of an intravenous solution to a patient. The configurations minimize the criticality of the alignment between the components. The cassette forms part of the flow path of the solution on its way to the recipient. The controller's valve member may stretch a membrane in the cassette and cause it to contact a flat surface surrounding the opening through which the fluid must flow. Alternately, the end of the valve member may be appreciably smaller than the opening, pass through it, and stretch the membrane until the latter contacts all of the opening's edge. The membrane meeting the edge of the opening in a closed loop prevents the flow of fluid through it. As a further possibility, the valve member may place the membrane in contact with one or more edges provided between two segments of a straight channel through which the solution flows.

9 Claims, 7 Drawing Figures

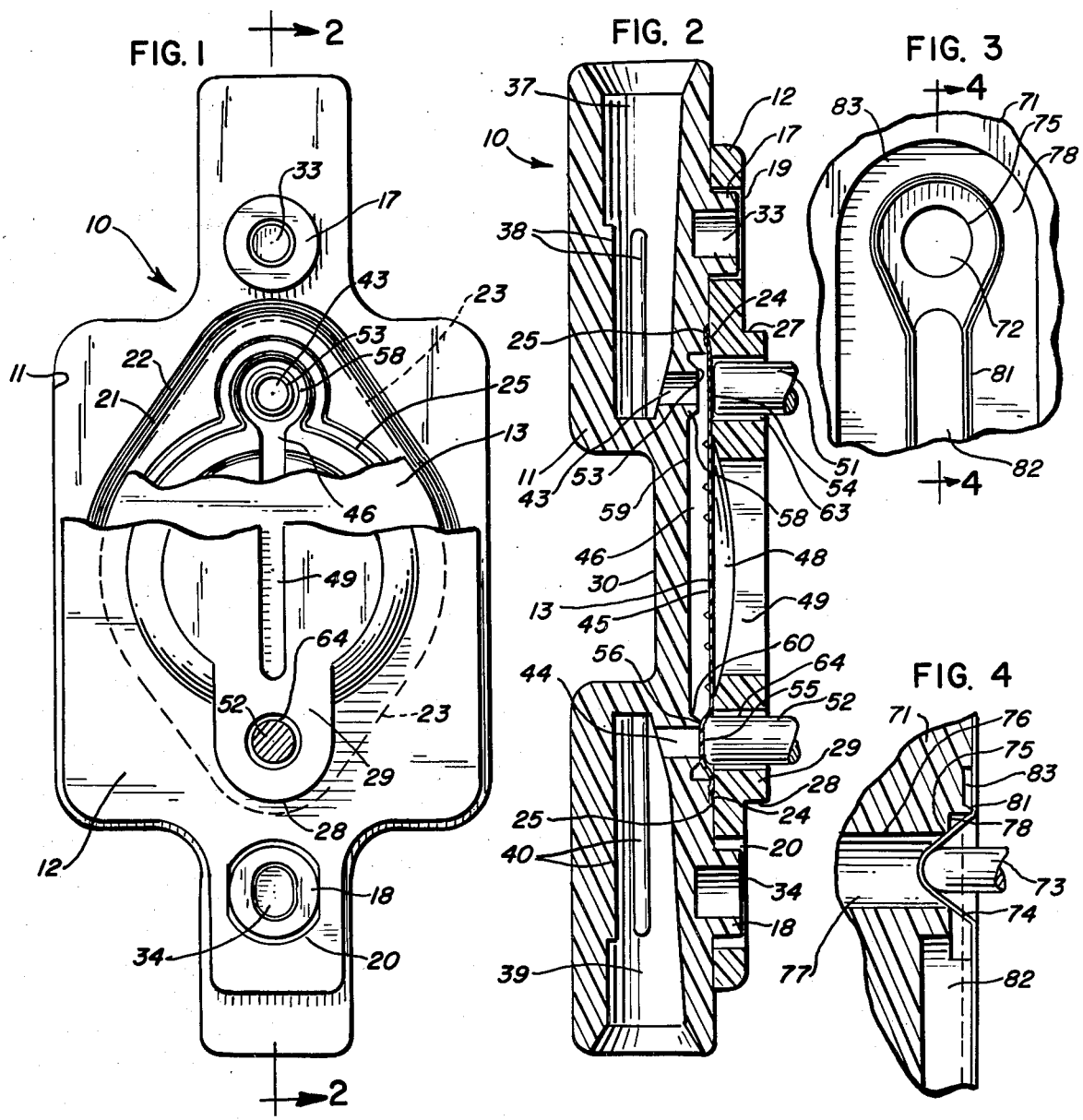
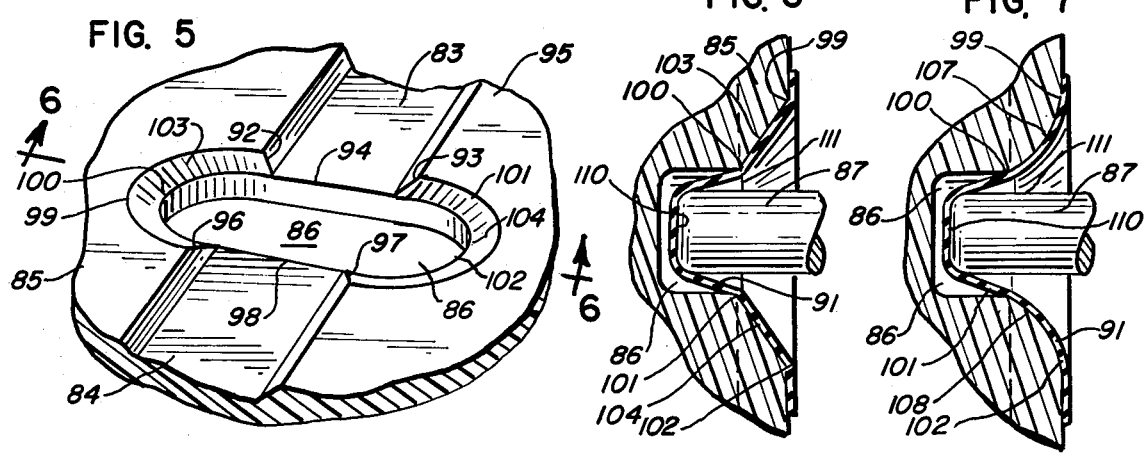

NONCRITICALLY ALIGNED VALVING DEVICES FOR FLOW RATE-LIMITING CASSETTES USED IN INTRAVENOUS SOLUTION ADMINISTERING EQUIPMENT

CROSS REFERENCES TO RELATED APPLICATIONS

The controller discussed in the subject application may make use of the Z-shaped bracket shown in the design patent application of Nick Zissimopoulos, entitled "Casette Holder and Transporter in a Fluid-Flow Limiting Device", U.S. application Ser. No. 878,965, filed Feb. 17, 1978, now abandoned. It may also utilize the mechanical components disclosed in the patent application "Improved Fluid-Flow Limiting Apparatus for Use with Intravenous Solution-Administering Equipment" of Nicholas Zissimopoulos, U.S. application Ser. No. 878,970, filed Feb. 17, 1978; the electronic circuitry of the patent application "Digital Electronic and Casette Sized for Intravenous Fluid-Flow Limiting Equipment" of Vincent L. Knigge and Norman Shim, U.S. application Ser. No. 878,846, filed Feb. 17, 1978; the electromagnetic device of the patent application "Low-Current E-Frame Electromagnet with a Permanent Magnet Armature for an I.V. Valving Controller" by Orest Hrynewycz, U.S. application Ser. No. 878,650, filed Feb. 17, 1978; and the electromagnet shape displayed in the design patent application "E-Frame Electromagnet Having a Permanent Magnet-Arm Armature" of Orest Hrynewycz, U.S. application Ser. No. 878,649, filed Feb. 17, 1978 and now abandoned. In addition to aspects of the above applications, the casette in the subject application may utilize the structure including the elastomeric membrane discussed in the patent application "Casette for Use with an I.V. Infusion Controller" of Scott F. Garrett, Lee K. Kulle, and William L. Rudzena, Ser. No. 878,966, filed Feb. 17, 1978; and the shape shown in the design patent application "Valvable Casette" of Lee K. Kulle and William L. Rudzena, Ser. No. 878,962, filed Feb. 17, 1978 and abandoned. All of these referenced applications have the same filing data as the subject application.

BACKGROUND

When a patient receives an intravenous solution, the flow rate of the solution into his blood stream must remain at or below a "safe" level. When the flow rate exceeds that level, the patient may suffer several deleterious consequences.

R. Scott Turner et al., in their U.S. Pat. No. 4,121,584 and entitled "Method and Apparatus For Controlling the Dispensing of Fluid", interpose a metering unit into the actual flow stream of the intravenous solution before it reaches the patient. They also provide a control unit which cooperates with the metering unit to provide a specified number of increments of fluid to the patient during particular time spans.

In operation, the control unit opens an inlet valve in the metering unit to allow fluid to enter a metering chamber having a defined maximum volume. After sufficient fluid has entered to fill that chamber, no further fluid can enter although the inlet valve may stay open. After the metering chamber has filled, however, the control unit closes the inlet and opens and outlet valve. The fluid within the metering chamber may then pass through the outlet to the patient.

After the metering chamber empties, the control unit closes the outlet valve and again opens the inlet to start another cycle of operation. The frequency of the cycles determines the maximum flow rate of solution received by the patient.

In the Turner, et al. patent, valving takes place by means of valve actuator pins which press a membrane against a land to effect closing of the inlet or outlet.

In accordance with this invention, an improved valving means is provided which requires less criticality of manufacture for providing effective inlet and outlet valves, for precise control of fluid flow in preferably a parenteral solution set.

SUMMARY

In this application, a fluid-flow limiting device has a metering means, or chamber, formed, in part, from a stretchable elastomeric membrane. A first section of substantially rigid material, such as plastic, also constitutes a part of the metering chamber.

To allow for the flow of fluid into and out of the metering chamber, the casette has a closable inlet and a closable outlet. Each has fluid communication with the chamber. The same membrane and section of plastic that constitute the metering chamber also form the inlet and outlet.

A second section of plastic then rigidly fuses to the first section discussed above. The two plastic sections envelop substantially all of the elastomeric membrane between them. The second section functions to limit the stretching of the membrane to a predetermined size in order to provide a metering chamber of a known maximum volume.

The second section of plastic also has an opening in the region of the inlet and another opening in the region of the outlet. These openings allow for the passage of the movable valve members on the controller to the membrane in order to stretch it and close off the inlet or the outlet, as appropriate.

To allow for less critically shaped components, the inlet may take the form of two chambers in fluid communication with each other. An orifice, formed in the first section of plastic, defines the opening between these two chambers. The edge of the orifice at the second chamber lies in a substantially flat plane.

This plane of the orifice has a normal which points outward from it from the first chamber to the second chamber. In operation, the valve member causes the membrane to contact either the orifice or the plastic around it. Accordingly, the plane of the orifice should have an orientation that allows valve member to cause the appropriate contact between it and the membrane. However, the valve member approaches the membrane through the opening in the second section of plastic in the region of the inlet. Thus, the normal from the plane of the orifice should make an angle of less than 90° relative to the direction passing from the orifice to the opening in the second piece of plastic. Stated in other words, this requirement implies that orifice faces the opening in the second section of plastic at least to some extent.

The outlet of the metering chamber appears very similar to the inlet. It has an orifice defining the opening between two chambers. The edge of the orifice at one of these chambers lies in a substantially flat plane. This plane, at least to some extent, faces the opening in the second piece of plastic in the region of the outlet. Specifically, the normal from the plane defined by the orifice points from the smaller of the two chambers towards the larger of the two chambers. It makes an angle of less than 90° relative to the direction from the orifice to the opening in the second piece of plastic lying near the outlet.

The metering chamber may constitute one of the chambers for both the inlet and the outlet. If so, it represents the larger chamber for both valves. In most instances, the orifice faces directly towards the direction from which the valve member moves to close the valve.

The valve member on the controller and the inlet and outlet on the casette may cooperate in two different ways to effect the desired valve closure. First, the valve member, may have an end with smaller cross-sectional area than the orifice. To close the valve, the end of the member actually moves through the plane of the orifice. In doing so, it first contacts the membrane and pushes a portion of it through the orifice. In this position, the membrane makes contact with the orifice all around the opening. The membrane, when in contact with the orifice, effectively blockades the passage of fluid between the two chambers. Consequently, it closes the valve.

Thus, to close the valve, the movable member need only fit inside of the orifice. The two need not fit each other very closely. In fact, a significant amount of space should exist between the orifice and the side of the valve member. Should the side of the valve member too closely approach the orifice, it could effect a shearing action upon the membrane and perhaps tear it. Accordingly, a casette using this type of valve mandates appreciable leeway between the side of the valve member and the edge of the orifice. Moreover, changing either of them within wide ranges cannot affect its operation. Consequently, the preciseness required in the manufacturing process drastically decreases. Nonetheless, the assuredness of the proper closure of the valve increases dramatically.

Since the valve member has a smaller cross-sectional area than the orifice, the opening in the second plastic piece in the region of the valve may also have a smaller area than the orifice. That results since the opening need only have a sufficient cross section to permit the valve member's passage.

The opposite relationship between the sizes of the orifice and the end of the valve member also produces an effective valving configuration which permits reasonable manufacturing tolerances. Specifically, the end of the valve member may have appreciably larger cross-sectional area than the orifice. The valve member then forces the membrane into contact with the plastic surface surrounding the orifice.

Specifically, to close the opening, the valve member must force the membrane to contact the plastic in a closed loop which includes the orifice itself. To provide the desired seal, the valve member actually exerts a force acting through the membrane against the plastic in a closed loop. The resulting hermetic seal keeps the fluid from passing through the orifice. Moreover, only the thickness of the membrane separates the valve member and the plastic behind the membrane.

To provide the seal around the orifice, the end of the valve member and the plastic near the orifice must possess shapes which will allow the firm seating of the former against the latter. Specifically, the plastic around the orifice must complement the configuration at the end of the valve member. Moreover, the chosen shape must also allow for a latitude in the actual location on the plastic that the valve member, covered by the membrane, contacts.

Most conveniently, both of the components may simply present a flat surface to each other. When the flat end of the valve member forces the membrane against the flat plastic surface around the orifice, the two can readily meet to close off the valve, this occurs without any particular regard to the exact relative location of the two components. If the orifice has a slightly altered location relative to the valve member, the two flat surfaces still meet with the membrane between them to provide the desired seal.

In this configuration, the surface of the plastic around the orifice lies in a flat plane. This flat plane also lies parallel to the plane of the orifice. The end of the valve also has a surface determining a flat plane lying parallel to the other planes just mentioned. Moreover, the elastomeric membrane itself generally assumes a flat shape in its least stretched configuration in the casette. The plane of the membrane, when so shaped, would also lie parallel to all of the other planes above.

To assure the sealing of the membrane near the orifice, the plastic around the orifice may take the form of a ridge with a flat top. This assures that the valve member will force the membrane into contact with the surface close to the orifice. The resulting contact provides a tight seal in the immediate vicinity of this opening.

Other shapes also permit the firm sealing of the membrane by the valve member against the plastic around the orifice. The shape of the plastic must, of course, complement that of the valve member. For example, where the end of the valve member has a convex surface, the plastic should appear concave. This still allows a latitude in the location of the valve member relative to the plastic around the orifice. Yet, it provides a firm seal of the membrane between the two of them.

Regardless of the shape, of course, the valve member must have a larger cross section than the orifice.

The valve configurations discussed above have involved stopping the flow of fluid passing from one chamber to another through an orifice. This arrangement accomplishes the objective of allowing greater latitude in the preciseness required of the manufactured parts while even increasing the assurance of their proper functioning in use.

Other configurations, however, can also achieve the same objectives while guaranteeing a secure closure for the valve. One such configuration in fact, allows the valving to operate between two sections of straight channel. Yet, it dispenses with the requirement that valve member placing the membrane in firm contact across all of the sides and the bottom of the channel.

A casette utilizing this valving configuration again has an elastomeric membrane and a section of rigid material, such as plastic, cooperating to form a metering chamber and the chamber's inlet and outlet. A second section of rigid material affixes to the first and sandwiches the membrane between them. It also has openings for the inlet and the outlet valving members of the controller.

The controller itself has moving means which places the valve members through the openings in the second section of plastic lying near the inlet and the outlet, as appropriate. The controller moves each of the valve members between two positions. The valve member, in one of these positions, lies closer to the first section of plastic than in the other position.

The first section of plastic, for each of the valves, provides an edge at a location where two surfaces, formed in this section of plastic, meet. At each point along the edge, the two surfaces have an angle between them through the plastic not greater than 150°. This provides at least some "sharpness" to the edge. The valve member then places the membrane in contact with the edge to provide the closure for the valve. Requiring contact with an edge represents a less severe manufacturing problem that contact along the sides and the bottom of the channel.

To create the requisite contact between the membrane and the edge, the edge should point towards the valve member when the latter occupies its "closed" configuration. It does so when the controller has moved it to the position where it lies closest to to first section of plastic with the edge. The edge, in fact, points towards the valve member when a line perpendicular to the edge and bisecting the angle between the two surfaces forming it would actually pass through the member. If the edge did not point in this direction at least to some extent, the valve member would have difficult in providing a sufficient contact between the membrane and the edge to close the valve.

To close, the membrane must reach all portions of the edge. To achieve this, the end of the valve member, when closest to the first section of plastic, should extend beyond all portions of the edge. Accordingly, when the valve member assumes its closed position, all of the edge should lie between the end of the valve member and the second section of plastic, through which the member moves to reach the membrane. If the edge lies beyond the end of the valve member, then the member could not force the membrane to contact it.

In operation, the valve member, to close the valve, places the membrane in contact with all of the edge. When the membrane makes this contact, it closes the opening and prevents the flow of fluid either to or from the metering chamber, as appropriate.

To open the valve, the controller retracts the valving member. The membrane then loses contact with at least a portion of the edge. The space between the edge and the membrane allows the flow of fluid.

BRIEF DESCRIPTIONS OF THE FIGURES

FIG. 1 gives an elevational view, partly in cross section through two different levels, of a casette having a valving configuration in which the valving member seats the elastomeric membrane on a flat surface surrounding an opening.

FIG. 2 gives a cross-sectional view along the line 2—2 of the casette of FIG. 1.

FIG. 3 has a front view of the inlet of a casette through which the valve member forces part of an elastomeric membrane to close it.

FIG. 4 gives a cross-sectional view along the line 4—4 of the casette segment shown in FIG. 3.

FIG. 5 displays a casette having an edge between two straight channel sections and which can function in blocking the passage of fluid between the two channel sections.

FIG. 6 has a cross-sectional view along the line 6—6 of the edge allowing for valve closure between two sections of channel.

FIG. 7 shows an edge similar to that of FIG. 6 but formed, in part, from a curved, instead of a flat, surface.

DETAILED DESCRIPTION

The casette 10 shown in FIGS. 1 and 2 includes the base section of plastic 11 and the cover plastic section 12. Sandwiched between them lies the elastomeric membrane 13. The circular protuberances 17 and 18 on the base section 11 pass through the openings 19 and 20 to properly align the two sections 11 and 12 together.

The opening 20 has a somewhat elongated, or oblong, configuration in the direction of the other opening 19. Since the circular configuration of the opening 19 snugly fits around the protuberance 17, it prevents any possible motion in the direction that the opening 20 would permit. Consequently, the lack of a circular outline for the opening 20 does not allow any motion between the two sections 11 and 12 of the casette 10. Yet, the oblong appearance of the opening 20 simply provides it with a latitude in the manufacturing process that will not adversely affect the final casette.

The base section of plastic 11 includes the ridge 21 which lies close to, but inside of, the well 22. To fuse the plastic sections 11 and 12 together, the former receives ultrasonic waves which condense at the ridge 21, causing it to melt. As the ridge 21 liquifies, it fuses the two plastic sections of 11 and 12 together. Any excess of plastic provided by the melted ridge 21, simply flows into the well 22, where it cannot interfere with the resulting casette 10.

The portion of the membrane 13 not shown in FIG. 1 has the dashed outline 23. During the ultrasonic fusing of the two sections 11 and 12 together, the membrane 13 could slip around as the base plastic section 11 received the vibrations. To prevent this, the cover slip 12 has the sharp edge 24, seen in FIG. 2. The edge 24, in particular, prevents the membrane 13 from moving out of position during the ultrasonic bonding. The well 25 in the base plastic section 11 provides room for the sharp ridge 24 and the membrane 13 which contacts it. After the fusion process, the ridge 24 has no further function.

The controller may utilize upper and lower arms which make contact with the upper edge 27 and the lower edge 28 of the protuberance 29 on the cover slip 12. A plate would sit against the surface 30 on the back of the base section of plastic 11. These arms and the plate roughly align the casette 10 in the controller.

To provide a fine alignment between the controller and the casette 10, the base section 11 has the indentations 33 and 34 located in the circular protuberance 17 and 18, respectively. The controller will then possess alignment pins which fits into the openings 33 and 34 to properly position the casette 10 for the valving operations directed by the controller.

As with the opening 20 in the cover slip 12, the indentation 34 has an elongated dimension pointing towards the other indentation 33. The controller's alignment pin that enters the indentation 33 snugly fits inside; the alignment pin entering the indentation 34 snugly fits between its sides but has some freedom of motion in the perpendicular direction. Again, that simply provides manufacturing tolerance while sacrificing no precision in the operation of the casette 10.

In operation, a rigid plastic tube, perhaps having the general configuration of a hypodermic needle, rigidly affixes to and extends out of the inlet channel 37. The ridges 38 limit the insertion of the plastic tube to the top of the channel 37 in order to allow for the normal flowing of fluid through the casette 10. The attendant inserts the plastic tube into the bottle of intravenous solution that the patient will receive. The flexible plastic tubing leading to the usual drip chamber fits into the bottom channel 39. The ridges 40 maintain this tubing near the bottom half of the channel 39. A squeeze fit between the tubing and the channel 39 suffices to keep the latter in place.

The controller operates cyclicly to provide fluid to the patient at a limited rate. At the beginning of a cycle, the controller closes both the inlet 43 and the outlet 44. At this point, the metering chamber 45, located between the membrane 13 and the portion of base plastic section 11 extending from the inlet 43 to the outlet 44 is substantially empty.

Fluid, however, generally remains in the groove 46 which can provide a direct conduit between the inlet 43 and the outlet 44 when the casette 10 does not operate under the guidance of a controller. When that occurs, some other device located on the tubing leading to the patient would then have to limit the flow rate.

Nonetheless, the fluid within the channel 46 does not otherwise affect the operation of the casette nor contribute to the volume of the metering chamber 45. Capillary action keeps fluid within the channel 46 even though the remainder of the metering chamber's contents have passed through the outlet 44.

To continue the operating cycle, the controller opens the inlet 43 and allows the metering chamber 45 to fill. As it does, the membrane 13 expands until it contacts the concave surface 48 formed in the cover plastic slip 12. The concave surface 48 limits the expansion of the membrane 13 and, thus, provides the metering chamber 45 with a definite volume.

When the metering chamber 45 has filled, the controller closes the inlet 43 and subsequently opens the outlet 44. The fluid in the metering chamber 45 then flows through the outlet 44 and the outlet channel 39 and to the patient. The slot 49 in the cover slip 12 allows for the equalization of air pressure as the membrane 13 expands and contracts while the metering chamber 45 fills and empties, respectively.

When the metering chamber 45 has emptied, the controller closes the outlet 44 and begins a new cycle of operation. The frequency of the operating cycles determines how many volumes of fluid equal to the contents of the metering chamber 45 the patient will receive over a period of time. The attendant may generally alter that amount, within preset limits, through an adjustment on the controller.

FIG. 2 shows the casette 10 with the inlet 43 opened and the outlet 44 closed. This represents the configuration that allows the metering chamber 45 to fill with the intravenous solution before passing it to the patient. During this portion of the cycle, the controller has retracted the movable inlet valve member 51 and extended the movable outlet valve member 52. As the inlet valve member 51 retracts, it allows the membrane 13 to contract and move off the valve face 53 of the inlet 43. The fluid from the inlet channel 37 then flows between the inlet valve face 53 and the membrane 13 to enter the metering chamber 45.

FIG. 2 shows that the flat bottom 54 of the valve member 51 has an appreciably larger surface area than the size of the inlet opening 43. This allows a significant latitude in the exact location of the valve member 51 relative to the inlet 43 which can still seal the membrane 13 between the valve face 53 and the valve member's bottom 54. Thus, the configuration of the flat valve 53 and the flat bottom 54 of the member 51 allows a latitude in the manufacturing process which produces the base section of plastic 11. Yet, it assures the complete closure of the inlet 43 when required in the operating cycle.

The outlet valve member 52, in FIG. 2, has moved towards the base section of plastic 11 to close the outlet 44. To do so, the flat bottom 55 of the valve member 52 places the membrane 13 in contact with the flat valve face 56 of the outlet 44. Fluid from the metering chamber 45 cannot then pass into the outlet 44 to flow to the patient.

As a result of the sloping surface 58, the valve face 53 lies closer to the valve member 51 than the remainder of the floor 59 of the channel 46. Similarly, the sloping surface 60 places the valve face 56 closer to the bottom 55 of the valve member 52. With the valve faces 53 and 56 thus projected outwards, the valve members 51 and 52 seal the membrane 13 and are very close to the openings 43 and 44. This provides a hermetic seal in a small closed loop which will prevent the passage of fluid through a closed valve.

The cover plastic slip 12 provides the openings 63 and 64 for the valve members 51 and 52. From above, the valve members 51 and 52 have a larger size than the inlet 43 and the outlet 44. As a result, the openings 63 and 64 must also have larger cross sectional areas than the inlet 43 and the outlet 44, respectively.

FIG. 3 shows a base section of plastic 71 having an inlet 72 through which fluid may pass. To close the opening 72, the valve member 73 forces the membrane 74 to contact the edge 75 of the opening 72. As shown in FIG. 4, the edge 75 represents the juncture of the wall 76 of the inlet channel 77 and the surface 78 which surrounds the opening 72. The exact juncture 75 between the surfaces 76 and 78 is slightly rounded so that it will not actually cut the membrane 74.

To place the membrane 74 in contact with the edge 75, the valve member 73 actually passes through the opening 72. In other words, part of the valve member 73 must cross the plane of the surface 78. When it does, it stretches the membrane 74 until the latter makes firm contact with all of the edge 75 to close the opening 72.

Other features of the base plastic section 71 include the ridge 81 to which the membrane 74 seals to provide the appropriate fluid channel. The surface 78 around the opening 72 provides a shallow channel for fluid passing through the inlet 77 until it reaches the deeper channel 82 which leads to the metering chamber, not shown in the figures. The groove 83 provides a location for the edge of the membrane located outside of the ridge 81 to sit.

FIGS. 5 and 6 show a valving device that operates between two straight channel sections 83 and 84 in a base section of plastic 85. Between the two straight channel sections 83 and 84, the base plastic section 85 includes the well 86 into which can fit the valve member 87. A controller would place the valve member 87 into the well 86 to prevent the flow fluid between the channel sections 83 and 84.

When the valve member 87 enters the well 86, it forces the membrane 91, seen in FIG. 6, to contact edges in the section of plastic 85. Specifically, in FIG. 5, the membrane 91 contacts the two sloping edges 92 and 93 as well as the bottom edge 94 which connects them. When the membrane contacts the edges 92, 93, and 94, it prevents the flow of fluid across the well 86 either to or from the straight channel section 83. This is particularly so, of course, since the membrane has a hermetic seal to the top 95 of the section of plastic 85.

Moreover, the membrane 91 achieves a double seal. With the valve member 87 inside of the well 86, the membrane 91 also seals against the side edges 96 and 97 and the bottom edge 98 connecting them. That prevents the flow of fluid between the channel section 84 and the well 86.

In addition, the membrane also seals against the circular edges 99 and 100 on one side of the well 86 and the edges 101 and 102 on the other side. That prevents leakage of any fluid into or out of the well 86 across the surfaces 103 and 104, respectively.

The valving configuration of FIG. 7 very closely resembles that of FIG. 6. However, the surface 107 between the edges 99 and 100, and the surface 108 between the edges 101 and 102 has a curved cross-section as opposed to the flat appearance of the surfaces 103 and 104 of FIG. 6. However, the edges 99 and 100 and 101 and 102 still permit the sealing of the membrane 91 by the valve member 87.

As FIGS. 6 and 7 show, the valve member 87 need only fit into the well 86. It does not have to closely approach the sides of the well 86 to provide the valving action. It must only force the membrane 91 to contact the edges discussed above. Accordingly, the configuration allows a significant latitude in the manufacturing process while still achieving the assured valving action between the channel sections 83 and 84.

The valve member 87, however, must enter the well 86 sufficiently far to bring the membrane 91 into contact with the relevant edges. It will generally do so if it lies closer to the edge than the distance between that same edge and the end 110 of the valve member. Thus, for example, the edge 100 lies closer to the side 111 of the valve member 87 than it does to its bottom 110.

Accordingly, what is claimed is:

1. In a device for controlling fluid flow through a flow path, a pair of alternatively operating, spaced valve means, controlling flow through said flow path, each valve means including a flow aperture defining an annular edge across which said flow path extends, a movable valve member comprising an elongated rod member, and a membrane positioned between said flow aperture and valve member, said valve member being adapted to move said membrane into and out of contact with said edge to respectively block and allow fluid flow through said flow path across said edge, the improvement comprising, in combination:
    said valve member having an outer transverse dimension which is smaller than the inner transverse dimension of said flow aperture, whereby said valve member is insertable into said flow aperture in spaced relation thereto, to draw said membrane into said sealing contact with said edge, said flow path entering the flow aperture across a first portion of the annular edge and exiting said flow aperture across a second portion of said annular edge.

2. The device of claim 1 in which each flow aperture is substantially circular.

3. The device of claim 1 in which said annular edge comprises an annular, rounded surface.

4. The device of claim 1 in which each spaced valve means utilizes different portions of a common membrane positioned between said flow aperture and valve member.

5. The device of claim 4 in which a metering chamber is positioned between said spaced valve means, said membrane occupying said metering chamber and adapted to expand outwardly to the limits of said metering chamber when filled with liquid and to contract to reduce the volume of said metering chamber when the chamber is emptied of liquid, said metering chamber being vented to permit said membrane to fully expand when filled with liquid.

6. The device of claim 1 as part of apparatus for controlling the administration rate of intravenous solution equipment.

7. The device of claim 1 in which the entrance and exit of the flow path to and from said flow aperture are opposed to each other.

8. In a device for controlling fluid flow through a flow path, a valve means controlling flow through said flow path, each valve means including a flow aperture defining an annular edge across which a flow path extends, movable valve member means comprising an elongated rod member, and a membrane positioned between said flow aperture and valve member means, said valve member means being adapted to move said membrane into and out of contact with said annular edge to respectively block and allow fluid flow through the flow path across said annular edge, the improvement comprising, in combination:
    said valve member means having an outer transverse dimension which is smaller than the inner transverse dimension of said flow aperture, whereby said valve member is insertable into said flow aperture in spaced relation thereto, to draw said membrane into sealing contact with said edge, said annular edge comprising a plurality of angled edge surfaces positioned parallel to said annular edge whereby said membrane is brought into sealing contact with said plurality of angled edge surfaces for improved sealing of said flow aperture, said flow path entering said flow aperture across a first portion of said annular edge and exiting said flow aperture across a second portion of said annular edge.

9. The device of claim 8 in which the entrance and exit of the flow path to and from said flow aperture are opposed to each other.

* * * * *